US006503536B2

United States Patent
Kalbe et al.

(12)

(10) Patent No.: US 6,503,536 B2
(45) Date of Patent: *Jan. 7, 2003

(54) GRANULATES OF HEXAHYDROPYRAZINE DERIVATIVES WHICH CAN BE ADMINISTERED ORALLY

(75) Inventors: Jochen Kalbe, Leichlingen (DE); Terence Hopkins, Tamborine (AU)

(73) Assignee: Bayer Aktiengesellschaft, Leverkusen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,858

(22) PCT Filed: Jul. 4, 1997

(86) PCT No.: PCT/EP97/03537

§ 371 (c)(1),
(2), (4) Date: Jan. 13, 1999

(87) PCT Pub. No.: WO98/03157

PCT Pub. Date: Jan. 29, 1998

(65) Prior Publication Data

US 2001/0055598 A1 Dec. 27, 2001

(30) Foreign Application Priority Data

Jul. 17, 1996 (DE) ......................................... 196 28 776

(51) Int. Cl.⁷ ................................................ A61K 9/14
(52) U.S. Cl. ........................ 424/489; 424/484; 424/485

(58) Field of Search ................................. 424/489, 484, 424/485, 486

(56) References Cited

U.S. PATENT DOCUMENTS

| 4,001,411 A | | 1/1977 | Seubert et al. ............... 424/250 |
| 4,447,414 A | * | 5/1984 | Gay et al. ..................... 424/81 |
| 4,661,489 A | | 4/1987 | Dorgan et al. ............... 514/211 |
| 5,068,112 A | * | 11/1991 | Samejima et al. .......... 424/495 |
| 5,824,653 A | | 10/1998 | Beuvry et al. ................ 514/30 |

FOREIGN PATENT DOCUMENTS

| EP | 0 252 407 | 1/1988 |

OTHER PUBLICATIONS

Chemical Abstracts, vol. 123, Nor. 14, Oct. 2, 1995, Abstract No 179458.
Ind. Eng. Chem. Res. vol. 35, (month unavailable) 1996, pp. 169–175.
Separations Technology, vol. 5, (month unavailable) 1995, pp. 213–228.
Journal of Liquid Chromatography, vol. 9(2&3), (month unavailable) 1986, pp. 341–368.

* cited by examiner

Primary Examiner—Thurman K. Page
Assistant Examiner—Blessing Fubara

(57) ABSTRACT

The present invention relates to the preparation of orally administrable granules of hexahydropyrazine derivatives by mixing the active compound in the presence of suitable solvents with hydrophobic carriers, if appropriate in the presence of auxiliaries, and converting the resulting mixture, if appropriate, into other ready-to-use forms.

2 Claims, No Drawings

GRANULATES OF HEXAHYDROPYRAZINE DERIVATIVES WHICH CAN BE ADMINISTERED ORALLY

The present invention relates to the preparation of orally administrable granules of hexahydropyrazine derivatives and also to granules which are prepared by this process.

Hexahydropyrazine derivatives, such as, for example, praziquantel and epsiprantel, are known (see U.S. Pat. No. 4,001,411, EP-A 134,984). Because of the bitter taste of the active compounds, a simple oral administration to taste-sensitive animals, such as, for example, cats, is not easily possible. Likewise, it is not possible to convert the active compounds by customary methods of taste masking, such as salt formation with embonic acid or binding to ion exchangers, into orally administrable compositions. Experience has shown that even by taste masking with flavors or using encapsulated formulations, it is not possible to obtain compositions of these active compounds which can be administered orally to cats.

It is known that hexahydropyrazine derivatives, such as, for example, praziquantel, can be separated into their enantiomers by column chromatography using chiral packing materials, such as, for example, cellulose triacetate (see Lim Beegim, Ching, Chibun, Industrial & Engineering Chemnistry Research, Vol 35, 1996, 169–175; Lim Beegim, Ching, Chibun, Separations Technology, Vol 5, 1995, 213–228; Blaschke G, Journal of Liquid Chromatoraphy, Vol 9/2–3, 1986, 341–368). This separation is effected owing to the different weak interaction between the column packing and the enantiomers of the active compound. There are no indications that it is possible in this manner to obtain active compound/carrier complexes which have a neutral taste.

It has now been found that orally administrable formulations of hexahydropyrazine derivatives are obtained by mixing the active compound in the presence of suitable solvents with hydrophobic carriers, if appropriate in the presence of auxiliaries, and converting the resulting mixture, if appropriate, into other ready-to-use forms.

By the process according to the invention, hexahydropyrazine-derivative-containing granules are obtained which can be administered orally without problems even to animals which normally refuse hexahydropyrazine-derivative-containing formulations because of their bitter taste.

To prepare the granules according to the invention, it is sufficient to mix active compound and solvent separately or an active compound solution with the hydrophobic carrier to give granules which contain the active compound. Furthermore, it was surprising that the granules prepared in this manner are accepted orally without hesitation even by taste-sensitive animals.

The granules comprise the components:
hydrophobic carrier 80 to 99.9% by weight,
hexahydropyrazine derivatives 0.1 to 20% by weight,
if appropriate further auxiliaries.

Hexahydropyrazine derivatives are known from U.S. Pat. No. 4,001,411, EP-A 13498, EP-A 185 012. The structural formulae and the individual compounds which are mentioned therein are expressly incorporated herein by reference.

Particular mention may be made of:
praziquantel (2-cyclohexylcarbonyl)-1,3,3,6,7-11b-hexahydro-4H-pyrazino[2,1-a]-isoquinolin-4-one and
epsiprantel 2-(cyclohexylcarbonyl)-2,3,6,7,8,12b-hexahydro-pyrazino[2,1-a]benzazepin-3(1H)-one.

Hydrophobic carriers which may be mentioned are: cellulose esters, such as cellulose triacetate, cellulose 2,5-acetate, cellulose propionate, cellulose butyrate, hydrophobicized silica gels, such as, for example, the reveresed phase phases RP2(-dimethyl), RP4(-butyl), RP8(-octyl), RP18(-ocetadecyl), RP-phenyl, RP-nitrile, which are used in column chromatography, talc, bentionite and dimethyldioctylammonium bentionite (bentionite 34).

Preference is given to cellulose acetate.

Further anthelminthically active compounds may be added to the granules according to the invention, for use at an application rate per kg of 0.1 to 20 mg, preferably of 1 to 10 mg, particularly preferably of approximately 5 mg.

Such active compounds which may be mentioned are phenylguanidines, such as febantel or netobimin; benzimidazoles, such as fenbendazole, albendazole, oxibendazole, oxfendazole, mebendazole, tricabendazole, mebendazole, fenbendazole, parbendazole, luxabendazole; tetrahydropyrimidines, such as pyrantel, morantel, oxantel; ivermectines and avermectines such as ivermectin, abamectin, moxidectin, doramectin; milbemycines; levamisole, tetramisole; cyclic depsipeptides such as PF 1022.

To prepare the granules according to the invention, other auxiliaries such as preservatives, antioxidants, photostabilizers, colorants, absorption-promoting substances, disintegration-promoting substances, binders or lubricants and stabilizers may be added.

Suitable preservatives are, for example, benzyl alcohol, benzoic acid, p-hydroxybenzoic acid, propionic acid and its derivatives and salts and also sorbic acid and its derivatives and salts.

Suitable antioxidants are, for example, albumins; amino acids, ascorbic acid, its salts and derivatives; butylhydroxyanisole; butylhydroxytoluene; derivatized hydroquinones.

Suitable photostabilizers are, for example, derivatives of aromatics, compounds with a suitable absorption wavelength.

Suitable colorants are, for example, pigments, such as, for example, iron pigments, water-soluble colorants or colorants soluble in organic solvents.

Suitable bioabsorption-promoting substances are, for example, fatty acid, fatty acid esters and mixtures thereof, fatty alcohols, lecithin, bile acid salts.

Suitable stabilizers are, for example, sodium sulphite, EDTA and its salts.

Suitable lubricants are, for example, magnesium stearate, stearic acid, talc, bentonites; suitable disintegration-promoting substances are, for example, starch or cross-linked polyvinylpyrrolidone, suitable binders are, for example, starch, gelatin or linear polyvinylpyrrolidone and also dry binders such as microcrystalline cellulose.

The process according to the invention is carried out by mixing the active compounds and carriers in the presence of solvents. The order in which the components are added is not crucial. The solvents used are usually evaporated again during the preparation of the granules.

Thus, the carrier and auxiliary components can be charged initially in a conventional mixer and mixed. To this mixture, active compound is added in the form of its solution, and mixed.

Suitable solvents for the active compounds are, for example:

Mono- or polyhydric alcohols, such as methanol, propylene glycol, ethanol, isopropyl alcohol, ketones, such as acetone, aromatic and non-aromatic hydrocarbons, such as toluene, xylene, ligroin, ethyl acetate, water THF, methylene chloride, dioxane.

The concentration of the active compound (salt) solution is from 0.5 to 50%; preferably 10 to 40%.

The individual components can be mixed in any type of mixer. For example, high intensity mixers having chopping devices are particularly suitable for preparing a homogeneous mixture. The solutions employed or water are added to the dry mixture in any order, including alternately, continuously or batchwise, by tipping, pouring, spraying or atomizing.

The moist mixture is processed further and, for example, grated, dried, then, for example, sieved or micronized.

Likewise, granulation using the fluidized-bed process is a suitable method of preparation. For this purpose for example the solutions are sprayed onto the moving mixture using one or more nozzles and, if desired, dried in the process.

If particularly small particles are required, micronizing may be an option (for example by using an air impact, bead or trituration mill).

The granules prepared according to the invention can be admixed with other carriers, in foodstuff applications these can be for example single feeds or mixtures thereof. Such formulations can be extruded or pelletized in powder form, dry or moist. They can also be applied dry on food pellets. The addition of a binder may be useful. Suitable binders are, for example, vegetable, animal or synthetic oils, fats, fatty acids, fatty alcohols, waxes, gelatin. The granules prepared according to the process of the invention can also be incorporated into moist pellets. Such pellets may comprise animal matter (for example moist pellet).

The granules prepared according to the invention can, inter alia, also be filled into capsules, the capsule wall being made of hard or soft gelatine. The capsule can, if appropriate, be enteric-coated.

The granules prepared according to the invention can also be used for preparing other orally administrable formulations, such as oral solutions, concentrates for oral administration after dilution;

emulsions and suspensions for oral administration;

pastes or preparations in which the formulation is processed in a semi-solid base or in an oil-in-water or water-in-oil emulsion base;

solid preparations such as powders, premixes or concentrates, pellets, extrudates, tablets, boluses, capsules;

or combinations of the forms mentioned.

The formulations according to the invention have favourable toxicity to warm-blooded animals and are suitable for controlling pathogenic endoparasites which occur in pets, such as, for example, cats and dogs. In this connection, they are active against all or individual stages of development of the pests and also against resistant and normally sensitive species. The pathogenic endoparasites include cestodes, trematodes, nematodes, Acantocephalae, in particular:

From the order of the Pseudophyllidea, for example Diphyllobothrium spp., Spirometra spp., Schistocephalus spp.

From the order of the Cyclophyllidea, for example Mesocestoides spp., Anoplocephala spp., Paranoplocephala spp., Moniezia spp., Taenia spp., Echinococcus spp., Hydatigera spp., Diorchis spp., Dipylidium spp., Joyeuxiella spp., Spyrometra spp.

From the subclass of the Digenea, for example Schistosoma spp., Fasciola spp., Dicrocoelium spp., Opisthorchis spp.

From the order of the Enoplida, for example Trichuris spp., Capillaria spp., Trichinella spp.

From the order of the Rhabditia, for example Micronema spp., Strongyloides spp.

From the order of the Strongylida, for example Stronylus spp., Triodontophorus spp., Oesophagodontus spp., Trichonema spp., Gyalocephalus spp., Poteriostomum spp., Cyclicocyclus spp., Stephanurus spp., Ancyclostoma spp., Uncinaria spp., Cyathostomum spp., Metastrongylus spp., Dictyocaulus spp., Muellerius spp., Protostrongylus spp., Elaphostrongylus spp., Parelaphostrongylus spp., Crenosoma spp., Paracrenosoma spp., Filaroides spp., Parafilaroides spp., Marshallagia spp., Hyostrongylus spp., Ollulanus spp., Craterostomum spp., Cyclicodontophorus spp., Hyalocephalus spp., Cylindropharynx spp., Caballonema spp., Elaeophorus spp., Dirofilaria spp., Onchocerca spp., Setaria spp.

From the order of the Oxyurida, for example Oxyuris spp., Enterobius spp.

From the order of the Ascaridia, for example Ascaris spp., Toxascaris spp., Toxocara spp., Parascaris spp., Probstmangria spp.

From the order of the Spirurida, for example Thelazia spp., Habronema spp., Draschia spp., Dracunculus spp.

The compositions according to the invention additionally have favourable toxicity to warm-blooded animals and are suitable for controlling pathogenic endoparasites which occur in animal keeping and animal breeding, in productive animals, breeding animals, zoo animals, laboratory animals, experimental animals and pets. In this connection, they are active against all or individual stages of development of the pests and also against resistant and normally sensitive species. By controlling the pathogenic endoparasites, disease, mortality and reductions in productivity (for example in the production of meat, milk, wool, hides, eggs, honey, etc.) should be decreased, so that more economical and simpler animal keeping is possible by the use of the active compounds.

The productive and breeding animals include mammals, such as, for example, cattle, horses, sheep, pigs, goats, camels, water buffalo, donkeys, rabbits, fallow deer, reindeer, fur-bearing animals, such as, for example, mink, chinchilla, racoon, birds, such as, for example, hens, geese, turkeys, ducks, ostrich.

The fish include productive and breeding fish, fish for aquariums and ornamental fish of all ages which live in fresh water, salt water and brackish water. The productive and breeding fish include, for example, carp, eel, trout, white fish, salmon, bream, roach, rudd, chub, sole, plaice, halibut, Japanese yellowtail (Seriola quinqueradiata), Japanese eel (Anquilla japonica), red seabream (Pagurus major), seabass (Dicentrarchus labrax), grey mullet (Mugilus cephalus), pompano, gilthread seabream (Sparus auratus), tilapia ssp., chichlid species, such as, for example, plagioscin, channel catfish.

The pathogenic endoparasites include cestodes, trematodes, nematodes, Acantocephalae, in particular:

From the order of the Pseudophyllidea, for example Diphyllobothrium spp., Spirometra spp., Schistocephalus spp., Ligula spp., Bothridium spp., Diphlogonoporus spp.

From the order of the Cyclophyllidea, for example Mesocestoides spp., Anoplocephala spp., Paranoplocephala spp., Moniezia spp., Thysanosomsa spp., Thysaniezia spp., Avitellina spp., Stilesia spp., Cittotaenia spp., Andyra spp., Bertiella spp., Taenia spp., Echinococcus spp., Hydatigera spp., Davainea spp., Raillietina spp., Hymenolepis spp., Echinolepis spp., Echinocotyle spp., Diorchis spp., Dipylidium spp., Joyeuxiella spp., Diplopylidium spp.

From the subclass of the Monogenea, for example Gyrodactylus spp., Dactylogyrus spp., Polystoma spp.

From the subclass of the Digenea, for example Diplostomum spp., Posthodiplostomum spp., Schistosoma spp., Trichobilharzia spp., Ornithobilharzia spp., Austrobilharzia spp., Gigantobilharzia spp., Leucochloridium spp., Brachylaima spp., Echinostoma spp., Echinoparyphium spp., Echinochasmus spp., Hypoderaeum spp., Fasciola spp., Fasciolides spp., Fasciolopsis spp., Cyclocoelum spp., Typhlocoelum spp., Paramphistomum spp., Calicophoron spp-, Cotylophoron spp., Gigantocotyle spp., Fischoederius spp., Gastrothylacus spp., Notocotylus spp., Catatropis spp., Plagiorchis spp., Prosthogonimus spp., Dicrocoelium spp., Eurytrema spp., Troglotrema spp., Paragonimus spp., Collyriclum spp., Nanophyetus spp., Opisthorchis spp., Clonorchis spp., Metorchis spp., Heterophyes spp., Metagonimus spp.

From the order of the Enoplida, for example Trichuris spp., Capillaria spp., Trichomosoides spp., Trichinella spp.

From the order of the Rhabditia, for example Micronema spp., Stronglyoides spp.

From the order of the Strongylida, for example Stronylus spp., Triodontophorus spp., Oesophagodontus spp., Trichonema spp., Gyalocephalus spp., Cylindropharynx spp., Poteriostomun spp., Cyclococercus spp., Cylicostephanus spp., Oesophagostomum spp., Chabertia spp., Stephanurus spp., Ancyclostoma spp., Uncinaria spp., Bunostomum spp., Globocephalus spp., Syngamus spp., Cyathostoma spp., Metastrongylus spp., Dictyocaulus spp., Muellerius spp., protostrongylus spp., Neostrongylus spp., Cystocaulus spp., Pneumostrongylus spp., Spicocaulus spp., Elaphostrongylus spp., Parelaphostrongylus spp., Crenosoma spp., Paracrenosoma spp., Angiostrongylus spp., Aelurostrongylus spp., Filaroides spp., Parafilaroides spp., Trichostrongylus spp., Haemonchus spp., Ostertagia spp., Marshallagia spp., Cooperia spp., Nematodirus spp., Hyostrongylus spp., Obeliscoides spp., Amidostomum spp., Ollulanus spp.

From the order of the Oxyurida, for example Oxyuris spp., Enterobius spp., Passalurus spp., Syphacia spp., Aspiculuris spp., Heterakis spp.

From the order of the Ascaridia, for example Ascaris spp., Toxascaris spp., Toxocara spp., Parascaris spp., Anisakis spp., Ascaridia spp.

From the order of the Spirurida, for example Gnathostoma spp., Physaloptera spp., Thelazia spp., Gongylonema spp., Habronema spp., Parabronema spp., Draschia spp., Dracunculus spp.

From the order of the Filariida, for example Stephanofilaria spp., Parafilaria spp., Setaria spp., Loa spp., Dirofilaria spp., Litomosoides spp., Brugia spp., Wuchereria spp., Onchocerca spp.

From the order of the Gigantorhynchida, for example Filicollis spp., Moniliformis spp., Macracanthorhynchus spp., Prosthenorchis spp.

The administration can be carried out both prophylactically and therapeutically.

The preferred use concentration of the active compounds in the mixtures according to the invention is from 1 to 300 mg, preferably from 5 to 50 mg, per kg of body weight.

EXAMPLE 1

90 g of cellulose triacetate are suspended in 1 liter of a 10% strength solution of praziquantel in ethanol, and the ethanol is slowly evaporated. This gives 100 g of a 10% strength praziquantel-containing powder.

What is claimed is:

1. Process for masking the taste of hexahydropyrazine derivatives comprising preparing orally administrable formulations of an active compound containing granules of hexahydropyrazine derivatives, comprising mixing the active compound in the presence of solvents with hydrophobic carriers, optionally in the presence of auxiliaries.

2. Granules, comprising the components:
hydrophobic carrier 80 to 99.9% by weight,
hexahydropyrazine derivatives 0.1 to 20% by weight,
optionally further auxiliaries.

* * * * *